United States Patent
Su et al.

(10) Patent No.: US 6,828,807 B2
(45) Date of Patent: Dec. 7, 2004

(54) BIOLOGICAL CELL TEST METHOD AND APPARATUS

(75) Inventors: Yo-Hsin Su, Kaohsiung Hsien (TW); Hsi-Lien Lu, Kaohsiung (TW); Ta-Chang Liu, Kaohsiung (TW); Hsun-Min Lung, Kaohsiung Hsien (TW); Long-Sun Huang, Taipei (TW); Shiming Lin, Taipei (TW); Der-Xing Liou, Banchiau (TW); Chien-Hsun Chen, Taoyuan (TW); Chih-Kung Lee, Taipei (TW)

(73) Assignee: Gongin Precision Industries Co., Ltd., Kaohsiung Hsien (TW)

( * ) Notice: Subject to any disclaimer, the term of this patent is extended or adjusted under 35 U.S.C. 154(b) by 15 days.

(21) Appl. No.: 10/334,910

(22) Filed: Jan. 2, 2003

(65) Prior Publication Data
US 2004/0130339 A1 Jul. 8, 2004

(51) Int. Cl.[7] .......................... G01R 27/08; G01N 27/02
(52) U.S. Cl. ........................ 324/692; 324/439; 324/703

(58) Field of Search ................................ 324/692, 693, 324/694, 696, 703, 439; 436/806, 807; 435/4, 287.1, 287.2, 287.3; 422/82.01

(56) References Cited

U.S. PATENT DOCUMENTS

| | | | | |
|---|---|---|---|---|
| 4,123,701 A | * | 10/1978 | Josefsen et al. | 324/448 |
| 5,432,086 A | * | 7/1995 | Franzl et al. | 435/286.2 |
| 6,169,394 B1 | * | 1/2001 | Frazier et al. | 324/71.4 |
| 6,448,794 B1 | * | 9/2002 | Cheng et al. | 324/693 |
| 6,476,622 B1 | * | 11/2002 | Robinson, Jr. | 324/692 |

* cited by examiner

*Primary Examiner*—Anjan K. Deb
(74) *Attorney, Agent, or Firm*—Birch, Stewart, Kolasch & Birch, LLP

(57) ABSTRACT

A biological cell test method and apparatus employs a conventional perforated cell carrier which has a plurality of holes. Each hole has two metal electrodes. A cell is disposed in the hole to contact the two electrodes. The electrodes are connected to electric current or voltage. The electric current or field flows from one electrode through the cell to another electrode. Through the inherent impedance, inductance or capacitance of the cell, the presence or property reactions of the cell may be detected.

11 Claims, 3 Drawing Sheets

BIOLOGICAL CELL TEST METHOD AND APPARATUS

FIELD OF THE INVENTION

The present invention relates to a biological cell test method and apparatus, and particularly a method that employs physical properties by applying electric field on animal or plant cells located in a plurality of arranged holes to interact with the impedance, inductance and capacitance characteristics of the cells under the flowing current or electric field to detect the presence or the property reactions of the cells.

BACKGROUND OF THE INVENTION

Biological technology is a technique that uses biological cells or their metabolic substances to manufacture products or improve animals, plants, microbes and their related products to improve the well-being of mankind. The technology has been applied to medicine, food, special chemistry, environment protection, oceanology, energy and agriculture. In response to biological research and development, such as mapping and sequencing of gene, biological chips have been developed and introduced to meet the demands of vast and fast reactions taking place during the research processes. The biological chip is an integration of functional biological material and micro mechanical electric techniques. The micro-electro-mechanical system techniques provide miniature planning and designs for the chip and offer a plurality of miniature zones in a small area to create reaction environments for functional biological materials.

In the past using the biological chip to do tests for biological cells usually is done by chemical methods. The biological cells are disposed in the holes of a perforated cell carrier, then a chemical agent is dispensed, and a fluorescent agent is added to see the reaction of the biological cells through an optical means. The chemical test method involves a lot of tedious procedures and requires many peripheral equipment. Moreover, the chemical test tends to destroy the tissues of the biological cell. And the preservation time of the biological cell also is shorter.

SUMMARY OF THE INVENTION

Therefore the primary object of the invention is to resolve the aforesaid disadvantages. The invention provides a novel test method and apparatus in addition to the conventional chemical methods of exploring the characteristics (properties) of the cells (animal and plant cells). The method of the invention employs a physical approach to focus on the cells that have inductance or capacitance properties. The reaction properties of the cell may be obtained with or without using the fluorescent agent during testing. The biological cell test may provide cell multi-properties with flexibility and effectiveness.

In order to achieve the foregoing object, the method of the invention employs a conventional perforated cell carrier which has a plurality of arranged holes. Each hole has two metal electrodes extending outside the hole. A cell is disposed in the hole to contact the two electrodes. As the cell has impedance, inductance or capacitance properties, when the two electrodes are energized with electric current or voltage, the electric current or electric field flows from one electrode through the cell to another electrode, as a result, electric reactions occur and the presence or absence of cell in the hole or property reactions of the cell may be detected.

The foregoing, as well as additional objects, features and advantages of the invention will be more readily apparent from the following detailed description, which proceeds with reference to the accompanying drawings.

DESCRIPTION OF THE PREFERRED EMBODIMENTS

Figure 1A:
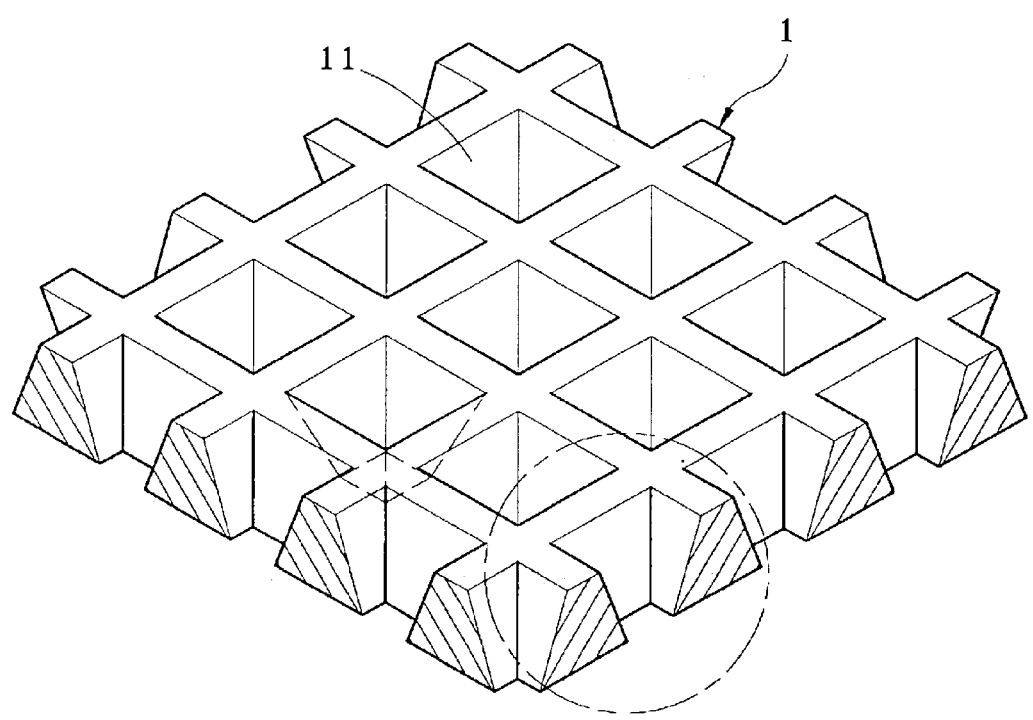
FIG. 1A is a perspective view of the perforated cell carrier of the invention.
Figure 1B:
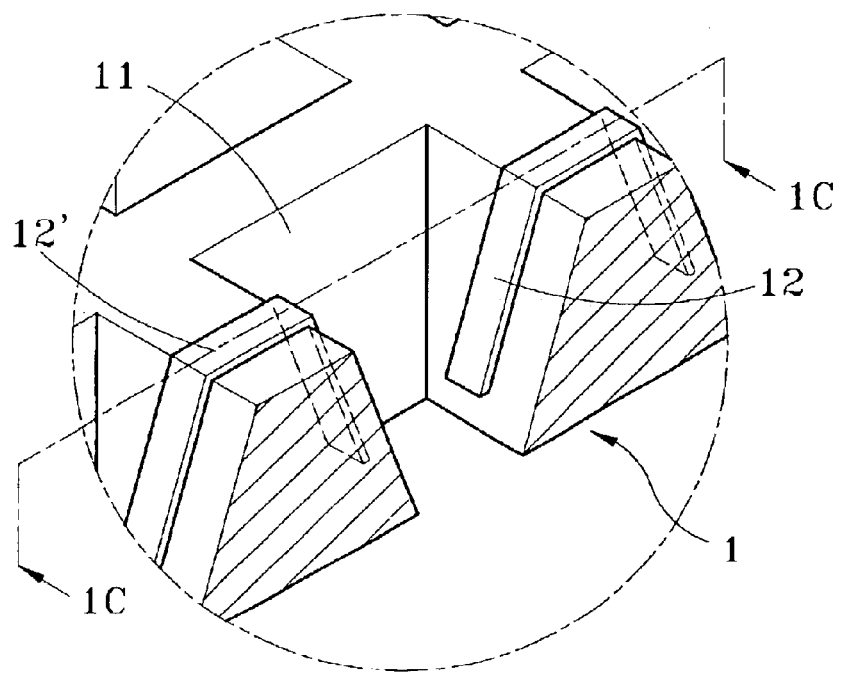
FIG. 1B is a fragmentary enlarged view of FIG. 1A.
Figure 1C:
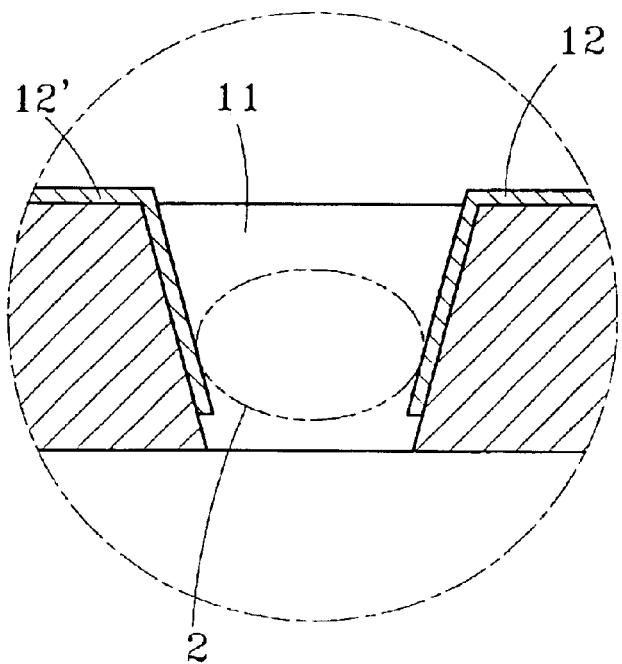
FIG. 1C is a cross section taken along line 1C—1C in FIG. 1B.

Refer to FIGS. 1A, 1B and 1C for the perforated cell carrier of the invention. The invention aims at providing a novel method and apparatus to test and explore the characteristics (properties) of biological cells (animal and plant cells) that is compatibly integrated, but different from the conventional chemical methods. The method employs a physical approach to target the cells that have inductance or capacitance properties. The reaction properties of the cells may be obtained with or without using the fluorescent agent during testing. The test is easier, more functional and more convenient.

The method of the invention employs a conventional perforated cell carrier 1. The perforated cell carrier 1 has a plurality of arranged holes 11 each is tapered from the upper side to the lower side. In the hole 11, there are two metal electrodes 12 and 12' that are extended from the inner side of the hole 11 to the exterior thereof. A cell 2 is disposed in the hole 11 to adjoin or contact the two electrodes 12 and 12'. The cell 2 has inherent impedance, inductance or capacitance properties. When the two electrodes 12 and 12' are energized with AC or DC electric current or voltage, the electric current or field flows from the electrode 12 through the cell 2 to another electrode 12'. As the cell 2 has electric properties, the presence of the cell 2 or the property reactions of the cell 2 may be detected physically without using the fluorescent agent.

In addition, using the physical approach that employs the electric properties to test the property reactions of the cell 2 is able to be integrated or independent of optical fluorescent means. Moreover, using the physical approach that employs the electric properties to test the cell 2 does not affect the tissues of the cell 2, therefore the cell 2 may be preserved for a longer period of time.

Figure 2:
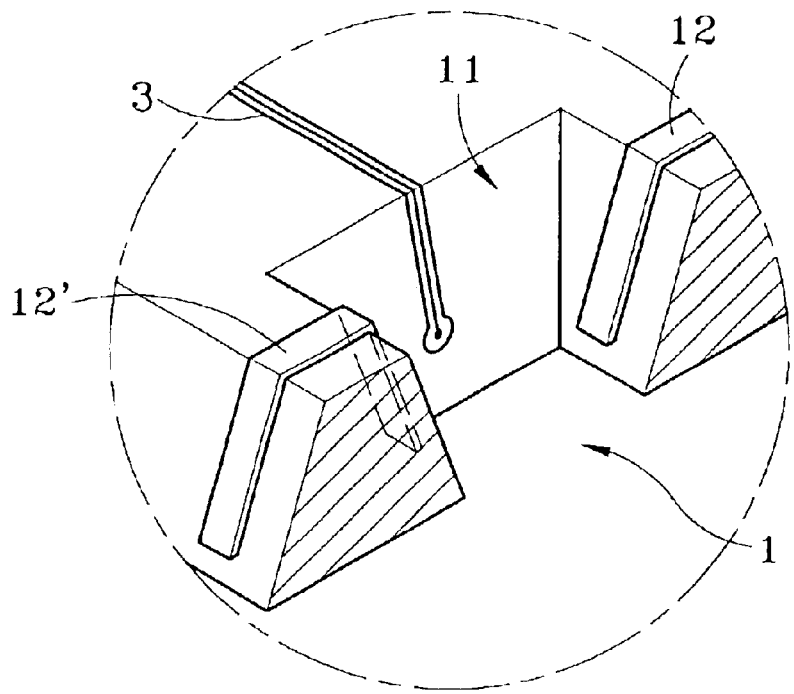
FIG. 2 is a schematic view of a second embodiment of the invention.

Refer to FIG. 2 for a second embodiment of the invention. On the perforated cell carrier 1, in addition to the two metal electrodes 12 and 12' located in the hole 11 for testing the physical electric properties of the biological cell 2, a heating means (electric wire) 3 may be added in the hole 11. Thus after the cell 2 is disposed in the hole 11, besides tested by connecting to electric current, the cell 2 may also be heated by the heating means 3 to test the reaction after heated.

Figure 3:
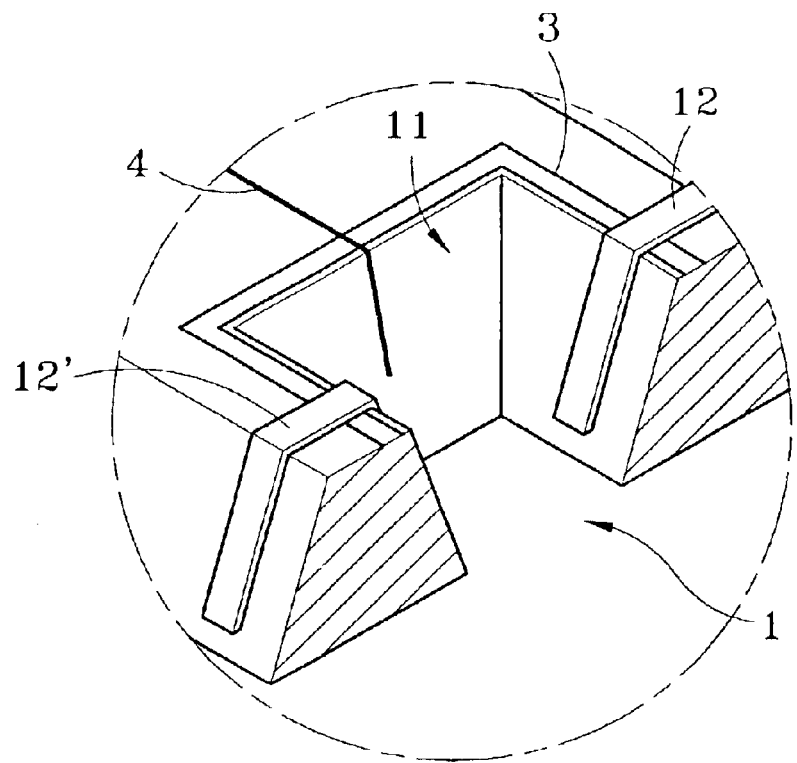
FIG. 3 is a schematic view of a third embodiment of the invention.

Refer to FIG. 3 for a third embodiment of the invention. It is substantially same as the embodiment set forth above. The difference is that the heating means 3 is located on the periphery of the hole 11, and a sensor device 4 is added to the perforated cell carrier 1. The sensor device 4 is for detecting the heating temperature of the cell 2 to prevent the cell 2 from being overheated and affected to ensure that the test of the cell 2 is performed effectively.

The foregoing heating means 3, besides being a heating wire, may also be an external heating device located outside the perforated cell carrier 1 to provide heating for the cell 2.

Furthermore, the sensor device 4 may also be an external sensor device rather than located on the perforated cell carrier 1.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A cell testing apparatus for testing cells through physical properties, comprising:
    a perforated cell carrier for holding cells having a plurality of holes arranged in a desired fashion; and
    electrodes located on the perforated cell carrier extending into the holes;
    heating means located on the perforated cell carrier and extending into the holes;
    wherein biological cells are located in the holes adjoining or in contact with the electrodes, the electrodes being connected to AC or DC electric current or voltage such that the electric current or an electric field passes through the biological cells to detect the presence of the cells or generate property reactions in the biological cells.

2. The cell testing apparatus of claim 1, wherein the cells are selected from the group consisting of animal cells and plant cells.

3. The cell testing apparatus of claim 1, wherein the electrodes are bipolar and connected to electric current or voltage.

4. The cell testing apparatus of claim 1, wherein the heating means is an electric heating wire.

5. The cell testing apparatus of claim 1, wherein the heating means is an external heating means.

6. The cell testing apparatus of claim 1 further having a sensor device located on the perforated cell carrier.

7. The cell testing apparatus of claim 6, wherein the sensor device is a temperature detection apparatus.

8. The cell testing apparatus of claim 6, wherein the sensor device is an external sensor device.

9. A method for testing cells through physical properties, comprising steps of:
    a. providing a perforated cell carrier which has a plurality of arranged holes, each of which has two metal electrodes located therein;
    b. providing heating means on the perforated cell carrier and extending into the holes.
    c. disposing a cell in each hole to contact the electrodes;
    d. connecting electric current to the electrodes so that the electric current or electric field flows within electrodes across the cell and the cell generates electrical properties resulting from its inherent impedance, inductance or capacitance.

10. The cell testing apparatus of claim 1, wherein said holes are of a size corresponding to said biological cells.

11. The cell testing apparatus of claim 1, wherein said heating means is in contact with said cells.

* * * * *